US010640578B2

(12) United States Patent
Krause et al.

(10) Patent No.: US 10,640,578 B2
(45) Date of Patent: May 5, 2020

(54) MODIFIED HYALURONIC ACID, METHOD FOR MAKING SAME AND USES THEREOF

(71) Applicant: Merz Pharma GmbH & Co. KGAA, Frankfurt am Main (DE)

(72) Inventors: Andreas Krause, Düsseldorf (DE); Alexander Linko, Frankfurt am Main (DE); Franck Villain, Paris (FR)

(73) Assignee: Merz Pharma GmbH & Co. KGaA, Frankfurt am Main (DE)

( * ) Notice: Subject to any disclaimer, the term of this patent is extended or adjusted under 35 U.S.C. 154(b) by 0 days.

(21) Appl. No.: 16/087,248

(22) PCT Filed: Mar. 21, 2017

(86) PCT No.: PCT/EP2017/056701
§ 371 (c)(1),
(2) Date: Sep. 21, 2018

(87) PCT Pub. No.: WO2017/162676
PCT Pub. Date: Sep. 28, 2017

(65) Prior Publication Data
US 2019/0100605 A1    Apr. 4, 2019

(30) Foreign Application Priority Data
Mar. 24, 2016    (EP) ..................................... 16000715

(51) Int. Cl.
| A61K 8/73   | (2006.01) |
| A61L 27/50  | (2006.01) |
| C08B 37/08  | (2006.01) |
| A61L 27/20  | (2006.01) |
| A61L 27/52  | (2006.01) |
| C08J 3/075  | (2006.01) |
| A61L 27/54  | (2006.01) |
| C08L 5/08   | (2006.01) |
| A61K 31/728 | (2006.01) |
| A61Q 19/08  | (2006.01) |

(52) U.S. Cl.
CPC .......... *C08B 37/0072* (2013.01); *A61K 8/735* (2013.01); *A61K 31/728* (2013.01); *A61L 27/20* (2013.01); *A61L 27/52* (2013.01); *A61L 27/54* (2013.01); *A61Q 19/08* (2013.01); *C08J 3/075* (2013.01); *C08L 5/08* (2013.01); *A61K 2800/91* (2013.01); *A61L 2300/402* (2013.01); *A61L 2430/34* (2013.01); *C08J 2305/08* (2013.01); *C08L 2203/02* (2013.01)

(58) Field of Classification Search
CPC combination set(s) only.
See application file for complete search history.

(56) References Cited

U.S. PATENT DOCUMENTS

| 2007/0066816 A1* | 3/2007 | Tsai ..................... C08B 37/0072 536/53 |
| 2010/0035838 A1* | 2/2010 | Heber ................... C08B 15/005 514/54 |
| 2012/0095206 A1  | 4/2012 | Chen et al. |
| 2012/0108674 A1  | 5/2012 | Gavard Molliard et al. |
| 2013/0196944 A1* | 8/2013 | Barg ....................... A61K 8/73 514/54 |

FOREIGN PATENT DOCUMENTS

| CN | 104194008 A   | 12/2014 |
| EP | 2537867 A1    | 12/2012 |
| WO | 2007083870 A1 | 7/2007  |
| WO | 2015149941 A1 | 10/2015 |

OTHER PUBLICATIONS

De Boulle et al. (Dermatol Surg 2013;39:1758-1766) (Year: 2013).*
Nobuhiko et al. (Journal of Controlled Release 1993;25(1-2):133-143 Abstract) (Year: 1993).*
Schante et al. (Carbohydrate Polymers 2011;85:469-489) (Year: 2011).*
International Search Report of International Patent Application No. PCT/EP2017/056701 dated Jun. 21, 2017.

* cited by examiner

*Primary Examiner* — Ernst V Arnold
(74) *Attorney, Agent, or Firm* — McBee Moore & Vanik IP, LLC

(57) ABSTRACT

The present invention generally relates to a modified hyaluronic acid (HA) and to a method for making same, more specifically to a (poly)glycerol-modified HA derivative prepared by grafting glycidol to HA. The present invention also relates to the use of the HA derivative for preparing a dermal filler composition, a hydrogel comprising cross-linked HA and the (poly)glycerol-modified HA derivative, and a method for preparing said hydrogel. Furthermore, the present invention relates to the use of the hydrogel as a cosmetic and/or aesthetic product, in particular as a dermal filler for tissue filling, replacing and/or augmenting.

17 Claims, No Drawings

MODIFIED HYALURONIC ACID, METHOD FOR MAKING SAME AND USES THEREOF

CROSS REFERENCE TO RELATED APPLICATIONS

This application is a National Stage entry of International Application No. PCT/EP2017/056701 filed 21 Mar. 2017, which claims priority to European Patent Application No. 16000715.9, filed 24 Mar. 2016.

BACKGROUND

Field of the Invention

The present invention generally relates to a modified hyaluronic acid (HA) and to a method for making same, more specifically to a (poly)glycerol-modified HA derivative prepared by grafting glycidol to HA. The present invention also relates to the use of the HA derivative for preparing a dermal filler composition, a hydrogel comprising cross-linked HA and the (poly)glycerol-modified HA derivative, and a method for preparing said hydrogel. Furthermore, the present invention relates to the use of the hydrogel as a cosmetic and/or aesthetic product, in particular as a dermal filler for tissue filling, replacing and/or augmenting.

Description of Related Art

Hyaluronic acid (HA) is a naturally occurring, non-immunogenic glycosaminoglycan composed of linked repeating units of N-acetyl-D-glucosamine and D-glucuronic acid ([α-1,4-D-glucuronic acid-β-1,3-N-acetyl-D-glucosamine]$_n$). Due to its high water-binding capacity and unique viscoelastic properties, HA is used in numerous applications, such as for drug delivery and tissue engineering, in therapy (e.g., as a supplement of joint fluid in arthritis or as a promoter of wound healing), and for cosmetic uses.

In the last several years, HA has been increasingly used in dermal fillers because they offer aesthetic improvements previously only achievable with surgery, but at lower cost and in a more convenient and safe manner. Today, HA is the most widely used degradable dermal filler material in both Europe and the USA. Since HA is quickly degraded and reabsorbed by the body, the HA is usually cross-linked to increase the in vivo residence time to about 6 to 18 months. The cross-linking can be conducted by a number of strategies, including diepoxy, carbodiimide-mediated, aldehyde, and divinyl sulfone crosslinking, with 1,4-butanediol diglycidyl ether (BDDE) being the "golden standard".

Dermal fillers based on crosslinked HA are used to restore facial volume, create youthful facial contours, add volume to lips and cheeks, fill in creases and lines, smooth out and reduce the appearance of fine lines, wrinkles, and folds (e.g., nasolabial folds, glabellar lines, marionette lines, and oral commissures), among others. The cosmetic/aesthetic treatment is performed in a nonsurgical setting and effects subside over time, as the hyaluronic acid is absorbed by the body.

It is further known in the art to modify HA in many different ways to alter the mechanical and/or chemical properties of HA-based fillers depending on the specific use. Chemical modifications are also used to prepare HA derivatives which are capable of in vivo polymerization, either spontaneously or in the presence of an external trigger like UV light or heat. The three functional groups of HA that can be modified are the primary and secondary hydroxyl groups, the glucuronic acid carbonic acid group, and the N-acetyl group (following deamination). Chemical modification of HA extends and improves the physical properties, thereby creating new degrees of freedom compared to the conventional BDDE cross-linked HA gels whose properties (e.g., high vs. low viscosity or monophasic/cohesive vs. biphasic/particulate) are primarily governed by the amount of HA and the degree of cross-linking.

US 2010/0035838 A1 discloses a combined cross-linking approach where HA is reacted in the presence of a BDDE cross-linking agent and glycidol as a masking agent to prepare a cross-linked HA gel having resistance to enzymatic degradation under physiological conditions. Since both epoxide compounds (i.e. BDDE and glycidol) are present during the cross-linking process, the process results in an undefined polymer network.

WO 2014/152632 A1 describes a HA-based composition suitable for use as a hydrophilic medical device coating. The composition is the reaction product of HA and a modified glycidol carbamate (GC) epoxide structure.

JP 5022618 B2 discloses a hydroxyalkylated HA having the following general formula:

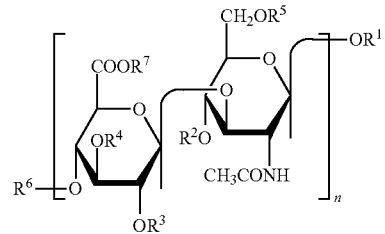

wherein $R^1$ to $R^6$ are hydrogen or an ether bonded hydroxyalkyl group, with the proviso that not all of $R^1$ to $R^6$ are hydrogen, $R^7$ is hydrogen or an alkali metal, and n is an integer of 1-10,000, wherein the hydroxyalkyl group is preferably one or more of a 2-hydroxypropyl group, a 2-hydroxybutyl group and a 2,3-dihydroxypropyl group. The hydroxyalkylated HA has a skin-moisturizing effect and is used as a humectant for topical formulations and moisturizers like cosmetic creams.

Moreover, it has been proposed to impart additional benefits to dermal filers by incorporating various substances, such as vitamins, polyols, mineral salts and the like, which exert skin health promoting effects. For example, US 2012/0108674 A1 describes a sterile, crosslinked HA hydrogel having specific rheological properties, which allows delayed release of glycerol over an extended period of time. However, there is still room for improvement for prolonging the continuous release of glycerol.

Although a variety of different dermal fillers with different physical and chemical characteristics are currently available, there is a continuous interest in new dermal filler products with improved properties. An ideal dermal filler should be well-tolerated, have as few side-effects as possible, and provide a reasonably long-lasting persistence (longevity), an effective volumizing capacity and ease of injection. In addition, a dermal filler desirably offers additional benefits such as incorporation of a local anesthetic for improved patient comfort or incorporation of vitamins, polyols, mineral salts and the like. Dermal fillers based on HA offer many of these desirable properties. HA has no antigenicity, exhibits excellent tolerance and, when crosslinked, has a good lifting capacity and is stable in the body for an extended period of time.

However, HA-based gels are often difficult to inject since the extrusion force required to inject a HA dermal filler through a fine needle are too high. Therefore, a lubrication phase, e.g., free (uncross-linked) HA, is often mixed with the crosslinked HA phase prior to sterilization in order to lower the extrusion force. Furthermore, HA fillers do not always have the desired optimal balance of properties, for example of longevity, lifting capacity and ease of injection, for a given application. Furthermore, the incorporation of additional substances may deteriorate the physical/chemical characteristics of the dermal filler gel product and/or may not provide the desired effects or only effects that are short-lived.

OBJECT OF THE INVENTION

In view of the above, the object of the present invention is the provision of an improved dermal filler which not only exhibits long-lasting in vivo persistence and high lifting capacity but also provides ease of injection and additional benefits.

SUMMARY

The above object is solved by the provision of a glycerol-modified HA derivative and its use in a dermal filler composition, comprising cross-linked HA and said glycerol-modified, uncross-linked HA as a "modified lubrication phase". This new type of HA-based dermal filler offers good longevity and has improved rheological properties, resulting in an excellent ability to create volume while still being easily injectable. Furthermore, the HA-based dermal filler offers the additional benefit of a slow and continuous release of glycerol molecules, resulting in the long-term supplementation of the skin with glycerol.

In a first aspect, the present invention provides a glycerol-modified hyaluronic acid (HA) derivative or a salt thereof having at least the primary hydroxyl group at the C6 carbon atom of all or a part of the N-acetyl-D-glucosamine units of HA modified into ether-bonded glycerol-containing moieties. Particularly, the ether-bonded glycerol-containing moieties are polyglycerol structures in the form of dendrimetric hyperbranched polyether-polyglycerol moieties.

In a second aspect, the present invention provides a method for making a hyaluronic acid (HA) derivative or salt thereof according to the present invention, comprising the steps of:

(a) solubilizing HA in an aqueous alkaline solution to obtain solubilized HA, (b) adding glycidol to the solubilized HA of step (a), (c) reacting glycidol and HA to obtain a glycerol-modified HA derivative and (d) purifying the glycerol-modified HA derivative.

Purifying step (d) leads to the preparation of the glycerol-modified HA derivative in a purified form suited for further use. The step commonly comprises a neutralization step and an isolation step to isolate/purify the glycerol-modified HA derivative from the reaction mixture of step (c).

In a third aspect, the present invention provides a hyaluronic acid (HA) derivative or salt thereof obtainable by the method for making a HA derivative or salt thereof according to the present invention.

The thus obtainable (poly)glycerol-grafted hyaluronic acid derivative is highly hydrophilic and is considered safe since the pending (poly)glycerol moieties are degraded in vivo into endogenous glycerol that is then metabolized in the liver and, thus, does not impair the excellent safety profile of hyaluronic acid.

In a fourth aspect, the present invention relates to the use of the hyaluronic acid (HA) derivative or salt thereof according to the present invention for preparing a dermal filler composition. Preferably, the HA derivative or salt thereof is added in uncross-linked form, in particular in the form of a solution, to a pre-formed crosslinked HA gel, notably a BDDE cross-linked HA gel, to obtain a dermal filler material having altered properties as compared to the crosslinked HA gel. Hence, the HA derivative or salt thereof may act like a "modified lubrication phase".

In a fifth aspect, the present invention provides a dermal filler composition comprising crosslinked hyaluronic acid (HA) or a salt thereof and a HA derivative or a salt according to the present invention.

In a sixth aspect, the present invention provides a method of preparing a dermal filler composition according to the present invention, comprising the steps of:

(i) providing a glycerol-modified hyaluronic acid (HA) derivative or a salt thereof according to the present invention, (ii) providing a crosslinked HA, (iii) combining the HA derivative and the crosslinked HA to obtain said dermal filler composition.

After combining the glycerol-modified HA derivative (Gly-HA) and the crosslinked HA, the resulting combination is typically homogenized to form a highly homogenous, and preferably cohesive, HA/Gly-HA gel. The obtained gel is then commonly sterilized, conveniently by moist heat such as by autoclaving.

In a seventh aspect, the present invention provides a kit, comprising a dermal filler composition according to the present invention, which comprises crosslinked HA or a salt thereof and a HA derivative or salt thereof, and, optionally, instructions for use.

In an eighth aspect, the present invention relates to the use of a dermal filler composition according to the present invention for cosmetic applications. Exemplary cosmetic applications include, but are not limited to, cosmetic treatments of facial lines, facial wrinkles, glabellar lines, nasolabial folds, marionette lines, buccal commissures, peri-lip wrinkles, crow's feet, subdermal support of the brows, malar and buccal fat pads, tear troughs, nose, lips, cheeks, peroral region, infraorbital region, facial asymmetries, jawlines, and chin.

In a ninth aspect, the present invention provides a method for replacing or filling of a biological tissue or increasing the volume of the biological tissue for cosmetic purposes, comprising administering to a subject in need thereof an effective amount of the dermal filler composition according to the present invention that comprises crosslinked HA or a salt thereof and a HA derivative or salt thereof as described herein.

Preferred embodiments of the present invention are set forth in the appended claims. Further embodiments and other objects, advantages and features of the present invention will become apparent from the following detailed description of the invention and the examples.

DETAILED DESCRIPTION OF A PREFERRED EMBODIMENT

It was found that the modification of HA by glycidol alters the properties of the resulting HA derivatives and leads to unique and interesting properties while maintaining the known desirable properties of HA such as its excellent viscoelastic (rheological) properties along with its biocompatibility and non-immunogenicity. In addition, a dermal filler comprising the HA derivative of the present invention and crosslinked HA provides a prolonged in vivo persistence and excellent volumizing capacity, and yet is easily injectable through fine needles.

Without being bound by theory, it is thought that the grafting of glycidol on HA yields a polyether-polyalcohol structure bearing a repeated glycerol moiety (sometimes also referred to as "polyglycidol structure") that imparts superior physical characteristics to the HA with respect to, e.g., humidity, swelling, cohesiveness and/or hydration. Specifically, it is believed that the formed polyether-polyglycerol structure is a dendrimeric, hyperbranched polyglycerol molecule that may be similar to the polyglycerol structure shown below (which, however, is not bonded to HA):

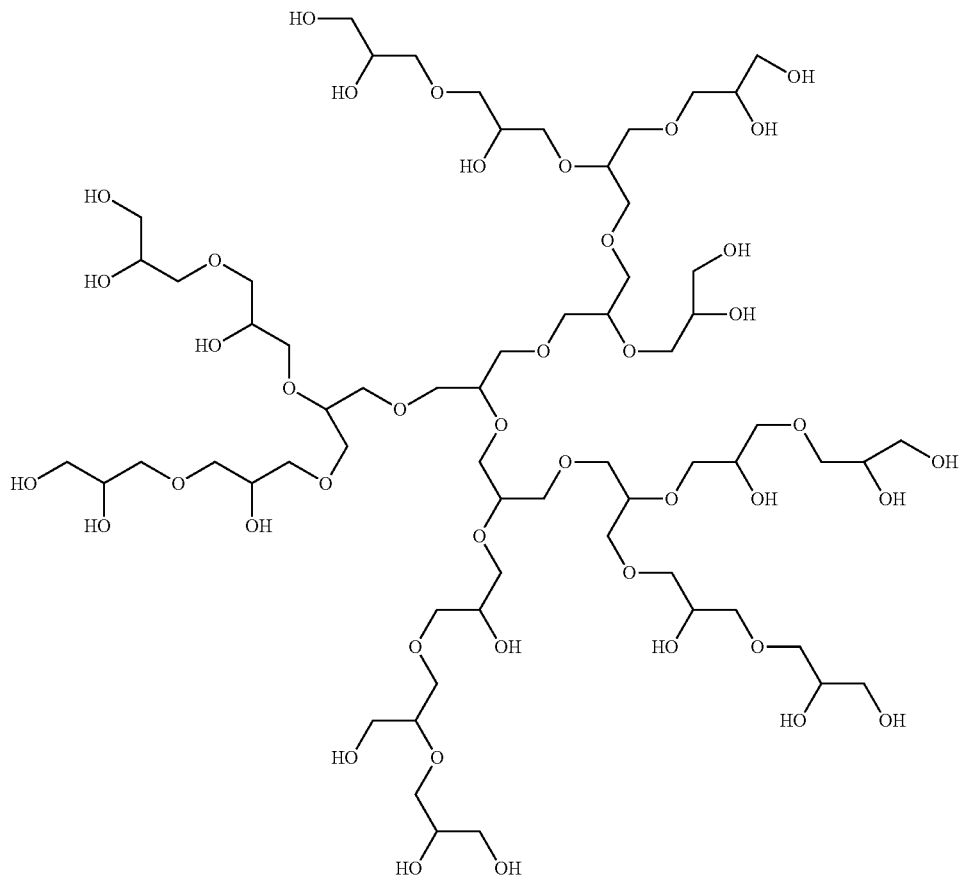 [SMILES: OCC(O)COCC(O)COCC(COCC(COCC(COCC(COCC(O)CO)OCC(O)COCC(O)CO)OCC(O)CO)OCC(COCC(COCC(O)COCC(O)CO)OCC(O)COCC(O)CO)OCC(O)COCC(CO)OCC(O)CO)OCC(O)COCC(O)CO]

Furthermore, again without being bound by theory, it is believed that the in vivo hydrolytic degradation of the polyglycerol structure leads to the steady or gradual release of glycerol into the surrounding tissue. Glycerol is an endogenous molecule and plays a major role in hydration of the skin, in skin elasticity and in repair of the epidermal barrier. However, it has been reported that the amount of glycerol in the skin decreases with age. The various beneficial effects of glycerol on the epidermis notably include hydration of the stratum corneum (the outermost layer of the skin), the barrier function of the skin, the mechanical properties of the skin, protection against irritant stimuli and acceleration of skin regeneration processes.

Once released, the glycerol migrates from the zone of dermal filler injection to the stratum corneum to exert its beneficial effects on the skin. In other words, it is believed that the glycerol-modified HA derivative, when injected into the skin, acts like a "reservoir" or "depot" of glycerol and provides for the continuous long-term supplementation of glycerol (i.e. supplementation for weeks, e.g., at least 4 weeks, and up to months). Thus, it is major advantage and additional benefit of the dermal filler composition of the present invention that the gradual in vivo release of glycerol from the glycerol-modified HA derivatives in the dermal filler hydrogel of the present invention can be used for skin moisturizing, reviving epidermal cellular activity, maintaining the mechanical properties of firmness and elasticity of the skin, stimulating skin regeneration and/or preventing skin aging.

Another advantage of the present invention is that it improves the physical and/or chemical properties of known cross-linked HA (cHA)-based dermal fillers without scarifying the existing desirable properties and performance of cHA-based dermal fillers since the HA derivatives of the present invention are added as a separate phase in uncrosslinked form to a (pre-existing) cHA-based hydrogel (e.g., Belotero®, Etermis®, etc.) prior to sterilization. Hence, this approach also allows maintaining the established production steps of known (e.g., BDDE) cross-linked HA fillers. Furthermore, this strategy allows to tailor and/or fine-tune the properties of a HA-based dermal filler required or desired for a given application.

In a first aspect, the present invention relates a glycerol-modified hyaluronic acid (HA) derivative or a salt thereof having at least the primary hydroxyl group at the C6 carbon atom of all or a part of the N-acetyl-D-glucosamine units of HA modified into ether-bonded glycerol-containing moieties.

Within the context of the present invention, the term "derivative", when used in connection with hyaluronic acid (HA), refers to HA that is derived from the natural HA by chemical modification such as etherification or esterification. As used herein, the term "hyaluronic acid" or "HA" means hyaluronic acid, hyaluronate, and any salt thereof, e.g., sodium hyaluronate. Also, the term "HA derivative", when used herein, is intended to encompass any salt thereof, in particular the sodium salt of the HA derivative.

The HA derivative of the present invention is "glycerol-modified", which refers to any covalently bound, in particular ether-bonded, glycerol-containing moiety. More specifically, the term "glycerol-modified", as used herein, means that HA is modified by a glycerol-containing moiety which is linked via an ether bond to the C6 carbon atom of all or a part of the N-acetyl-D-glucosamine units of HA. Furthermore, the term "glycidol-modified" or the like has the same meaning as, and is interchangeably used herein with, the term "glycerol-modified" or the like, unless otherwise stated.

The expression used herein that "all or a part" of the N-acetyl-D-glucosamine units of HA are modified is not intended to impose any particular limitation but merely reflects the fact that a chemical synthesis may not yield 100% of the desired reaction product. In other words, if only "a part" of the OH groups at C6 are modified into ether-bonded glycerol-containing moieties, this means that there are OH groups that have not undergone etherification and, thus, remain "free" primary OH groups.

Preferably, the glycerol-containing moieties of the glycerol-modified HA derivative according to the present invention are linked to the C6 carbon atom of N-acetyl-D-glucosamine units of HA in an amount such that the glycerol-modified HA derivative comprises between 1 and 100, preferably between 2 and 50, more preferably between 5 and 20, and most preferably between 10 and 20, of said glycerol-containing moieties per 100 repeating disaccharide unit of the HA. It is pointed out that, within the meaning of the present invention, this does not exclude that other functional groups of HA, i.e. COOH groups and other OH groups, in particular other (secondary) OH groups, are glycerol-modified, albeit in a much lesser extent. Hence, although the HA derivative according to the first aspect of the present invention refers to C6 etherification, it may be possible, and not explicitly excluded herein, to preferentially attach glycerol-containing moieties to any one of the other OH groups of the repeating disaccharide unit of HA. However, within the present invention, the polyglycerol-containing moiety is preferably only, essentially only or predominantly attached via an ether bond to the C6 carbon atom of GlcNac.

The term "glycerol-containing moiety", as used herein, refers to a moiety that is bonded to HA, preferably or predominantly via an ether linkage to the C6 carbon atom of N-acetyl-D-glucosamine units of HA (i.e. HA-C6$_{GlcNAc}$-O-"glycerol-containing moiety"), and may comprise or consist of a single glycerol unit (e.g., —O—CH$_2$—CHOH—CH$_2$—OH) or two or more ether-bonded glycerol units. The polyglycerol structure formed by said two or more glycerol units, in particular when formed of five or more glycerol units, may have, and typically has, the form of a dendrimetric hyperbranched polyglycerol structure (e.g., —O—CH$_2$—CHOR$^1$—CH$_2$—OR$^2$, wherein R$^1$ and R$^2$ are each independently a hydrogen atom or a branched or linear polyglycerol moiety, provided not both of R$^1$ and R$^2$ are hydrogen atoms, and wherein said branched or linear polyglycerol polyglycerol moiety may, e.g., comprise 1 to 50, 5 to 30 or 10 to 20 etherified glycerol units).

The term "glycerol unit", as used herein, refers to chemical groups having a glycerol skeleton and, more specifically, may refer to a —CH$_2$—CHOH—CH$_2$OH unit ("terminal unit", T), a —CH$_2$—CHOH—CH$_2$O— unit (linear unit, L), a —CH$_2$—CH(O—)—CH$_2$O— unit (branched or "dendritic" unit, D), and combinations thereof, which are all derived from glycerol, a three carbon and three hydroxyl group compound of formula HOCH$_2$CHOHCH$_2$OH. Thus, in case the "glycerol-containing moiety" consists of only a single glycerol unit, the structure is: HA-T. In case of two glycerol units, the structure is: HA-L-T, i.e. HA-(CH$_2$—CHOH—CH$_2$O—R) with R=T. In case of three glycerol units, the structure is: HA-L-L-T or HA-D(T)-T.

Within the present invention, the glycerol-containing moiety preferably contains n glycerol units, wherein n is at least 5, or at least 10 or at least 15. The upper limit of n is determined by the specific synthesis conditions used. Usually, n does not exceed 40 or 30 or 20 glycerol units. In accordance with the present invention, a glycerol-containing moiety having three or more glycerol units, preferably and predominantly have a branched or—in particular if n is equal or greater than 5—a hyperbranched polyglycerol structure.

The HA derivative of the present invention is generally derived from HA or a salt thereof having an average molecular weight in the range of $1.0 \times 10^4$ Da to $5.0 \times 10^6$ Da, preferably in the range of $1.0 \times 10^6$ Da to $4.5 \times 10^6$ Da, more preferably in the range of $2.0 \times 10^6$ Da to $4.0 \times 10^6$ Da. The HA average molecular weight may also range from $5 \times 10^4$ Da to $3.0 \times 10^6$ Da, further preferably from $1.0 \times 10^5$ Da to $2.0 \times 10^6$ Da or from $3.0 \times 10^5$ Da to $1.0 \times 10^6$ Da. The HA starting material for making the HA derivative of the present invention is not otherwise limited and may, for example, include a mixture of HA preparations having different average molecular weights, such as a first average molecular weight below $1.0 \times 10^6$ Da and a second average molecular weight of above $1.0 \times 10^6$ Da, wherein the difference between the first and second molecular weights is preferably more than $0.1 \times 10^6$ Da, more than $0.5 \times 10^6$ Da, or more than $1.0 \times 10^6$ Da.

Within the framework of the present invention, the average molecular mass of HA polymers is preferably determined by viscometry via the Mark-Houwink equation. The Mark-Houwink equation gives a relation between intrinsic viscosity ($\eta$) and the viscosity average molecular weight and allows determination of the average molecular weight of a polymer from data on the intrinsic viscosity and vice versa. Within the context of the present invention, the intrinsic viscosity is preferably measured according to the procedure defined in European Pharmacopoeia 7.0 (Hyaluronic Acid monograph No. 1472, January 2011). For calculation of the average molecular weight of HA from intrinsic viscosity data, the following Mark-Houwink is used within the framework of the present invention:

$$[\eta] = K \times M^a,$$

wherein [$\eta$]=intrinsic viscosity in m$^3$/kg, M=viscosity average molecular weight, K=$2.26 \times 10^{-5}$, and a=0.796. In accordance with the present invention, the intrinsic viscosity of the HA starting material usually ranges from 1.350 m³/kg (1350 m³/kg) to 4.500 m³/kg (4500 ml/g), especially from 2.0 m³/kg to 4.0 m³/kg.

Whilst the starting HA used for making the HA derivative of the present invention may have average molecular weights as indicated above, the final HA derivatives may have a lower average molecular weight due to the fact that the synthesis of the HA derivative is carried out under alkaline conditions in an aqueous solution. Thus, the HA (only the HA polymer part or the HA "backbone") of the HA derivatives of the present invention may have an average molecular weight of about $2.0 \times 10^3$ Da to $1.0 \times 10^6$ Da or $3.0 \times 10^3$ Da to $0.5 \times 10^6$ Da or $5.0 \times 10^3$ Da to $0.2 \times 10^6$ Da or $1.0 \times 10^4$ Da to $1.0 \times 10^5$ Da. The final HA derivative (i.e. the glycidol-substituted HA) typically has an average molecular weight of about $0.5 \times 10^6$ Da to about $3.5 \times 10^6$ Da, particularly $1.0 \times 10^6$ Da to $3.0 \times 10^6$ Da, more particularly $1.3 \times 10^6$ Da to $2.5 \times 10^6$ Da, and most particularly $1.5 \times 10^6$ Da to $2.0 \times 10^6$ Da, depending on the extent of grafted (poly)glycerol moieties and the chain length of a given HA derivative.

Although the Mark-Houwink relationship is not the same for HA and the corresponding HA derivative, the above-mentioned Mark-Houwink equation and parameters (K, a) may be used for determining the average molecular weight of the HA derivative of the present invention. The intrinsic viscosity of the HA derivative of the present invention may be in the range of 0.020 m³/kg (20 ml/g) to 1.500 m³/kg (1500 ml/g), in particular in the range of 0.100 m³/kg (100 ml/g) to 1.000 m³/kg (1000 ml/g). The complex viscosity of the HA derivative may range from 0.04 Pa·s to 1.0 Pa·s or from 0.1 Pa·s to 0.5 Pa·s.

In a second aspect, the present invention relates to a method for making a hyaluronic acid (HA) derivative or a salt thereof according to the present invention, comprising the steps of:

(a) solubilizing HA in an aqueous alkaline solution to obtain solubilized HA, (b) adding glycidol to the solubilized HA of step (a), (c) reacting glycidol and HA to obtain a glycerol-modified HA derivative and, (d) purifying the glycerol-modified HA derivative.

Within the context of the present invention, the method for making the hyaluronic acid derivative or a salt thereof may be based on a "grafting from" approach or a "grafting onto" approach, but is not specifically limited to a particular grafting approach.

In step (a), the HA (HA starting material) is solubilized. Preferably, the HA is first dissolved in an aqueous solution (e.g., distilled water) for a given time (e.g., 0.5 h to 12 h) to bring the HA into solution and to allow it to swell. Then, the pH of the mixture is adjusted to an alkaline pH (e.g., 9 to 12, in particular 10 to 11) by addition of a base (e.g., NaOH, preferably a NaOH solution). Then, in step (b), a given amount of glycidol (typically an excess amount, e.g., 2 equivalents, mol/mol) is added to the solubilized HA. The amount of HA present in the reaction mixture may be in the range of 10 mg/ml to 100 mg/ml or, particularly, in the range of 20 mg/ml to 50 mg/ml. In step (c), the mixture is allowed to react for a given time (e.g., 0.5 h to 5 h) at a given temperature (e.g., 40° C. to 55° C.). Finally, in step (d), the glycerol-modified HA derivative contained in the reaction mixture resulting from step (c) is purified.

In accordance with the present invention, step (d) of the method may comprises the sub-step (d1) of neutralizing a reaction mixture resulting from step (c) comprising the glycerol-modified HA derivative, or the sub-step (d2) of isolating the glycerol-modified HA derivative from the reaction mixture to obtain the glycerol-modified HA derivative in purified form, or both sub-steps (d1) and (d2). In sub-step (d1) neutralization may be effected by acidification using, e.g., an acid like hydrochloric acid. Conveniently, the isolation (which simultaneously includes a purification step) of sub-step (d2) may be carried out by dialysis and/or precipitation, as known to those skilled in the art.

In a third aspect, the present invention relates to a hyaluronic acid (HA) derivative obtainable by the method according to the present invention. Due to the grafted (poly)glycerol structures the HA derivative is highly hydrophilic. Furthermore, the hyperbranched polyglycerol structures are considered to reduce entanglements of HA polymers, thereby leading to lower viscosities in comparison to unmodified HA.

In a fourth aspect, the present invention relates to the use of the hyaluronic acid (HA) derivative or salt thereof according to the present invention for preparing a dermal filler composition. Preferably, the HA derivative or salt thereof is added in uncross-linked form, in particular in the form of a solution, to a pre-formed crosslinked HA gel, notably a BDDE cross-linked HA gel, to obtain a dermal filler material having altered properties as compared to the crosslinked HA gel. Hence, the HA derivative or salt thereof may act like a "modified lubrication phase".

As used herein, the term "dermal filler" broadly refers to a material designed to add volume to areas of soft tissue deficiency. The term "dermal filler" has the same meaning as, and is interchangeably used herein with, the term "soft tissue filler". This is, the term "dermal filler" is not intended to impose any restriction as to the location and type of injection other than a "soft tissue filler" suitable for or used in cosmetic/anesthetic applications. The term "composition", as used herein, is intended to mean a composition that is used or suitable for use as a dermal filler. A "dermal filler composition" within the meaning of the present invention is generally a substance that adds, replaces or augments volume under the skin leading to, e.g., smoothened skin wrinkles, augmented lips, improved skin appearance, or treated scars. It is generally used in the dermis area, such as below the epidermis or above the hypodermis and as such may be injected subcutaneously, hypodermically or intradermally, or some combinations.

According to the present invention, the dermal filler composition is commonly present in the form of a gel or hydrogel. The term "gel", as used herein, generally refers to a material having fluidity at room or body temperature between that of a liquid and solid. In addition, the term "gel" is intended to mean a material capable of absorbing water and, thus, may also be referred to as a "hydrogel" herein. Within the present invention, the dermal filler composition generally comprises a physiologically acceptable carrier fluid, particularly an apyrogenic isotonic buffer, more particularly a physiological saline solution or a buffered physiological saline solution.

Furthermore, the dermal filler composition of the present invention is generally "injectable". This means that the dermal filler composition is suitable for injection into the skin or other tissue in order to bring the soft tissue filler composition to the desired target site. An "injectable" composition within the meaning of the present invention can be dispensed from syringes under normal conditions under normal pressure. Moreover, the dermal filler composition of the present invention is preferably "sterile". Sterilization may be accomplished by subjecting the dermal filler composition, preferably after filling it into a syringe, to moist heat, e.g. by autoclaving.

In a fifth aspect, the present invention relates to a dermal filler composition according to the present invention which comprises crosslinked hyaluronic acid (HA) and a HA derivative in accordance with the present invention. The HA derivative is generally not crosslinked and used as a separate phase that is added to the (pre-existing) crosslinked HA phase.

In the context of the present invention, the crosslinked hyaluronic acid is not limited in any way and includes crosslinked hyaluronic acid prepared from a single hyaluronic acid or from two or more hyaluronic acids that differ in their molecular weight (see, e.g., US 2010/0316683 A1 or WO 2013/185934 A1, which are incorporated herein by reference). Also, within the scope of the present invention, the crosslinked hyaluronic acid may form a "polydensified" gel which is characterized by a variation of the degree of crosslinking within the gel, i.e. a "polydensified" gel has (at least) two different density levels with denser parts (higher degree of crosslinking) and less dens parts (lower degree of crosslinking).

Polydensified gels can be prepared, for example, by a first crosslinking reaction to crosslink first polysaccharide(s), followed by a second crosslinking reaction to crosslink second polysaccharide(s) to form a double-crosslinked gel. Said first and said second polysaccharide(s) may, for example, independently be the same hyaluronic acid or two different hyaluronic acids which differ in their average molecular weight (e.g., a low molecular weight and a high molecular weight hyaluronic acid). The double-crosslinking process (dynamic cross-linking technology) is known in the art and is described, for example, in EP 1 711 552 B1, which is incorporated herein by reference.

The crosslinked HA may be present in the composition in a concentration of of 0.1% to 4.0%, preferably of 0.5% to 3.5%, more preferably of 1.0% to 3.0% or 1.5% to 2.8%, and most preferably from 2.0% to 2.5% by weight/volume or by weight/weight (which is similar to weight/volume since the density of hydrogels is close to 1 g/ml). Within the present invention, the crosslinked hyaluronic acid may be prepared by crosslinking a single hyaluronic acid or by crosslinking a first hyaluronic acid and a second hyaluronic acid, and, optionally, at least one further hyaluronic acid, wherein the first, second and at least one further hyaluronic acid differ in their average molecular weights.

Within the context of the present invention, the HA preferably has an average molecular weight of $0.5 \times 10^6$ Da to $4.0 \times 10^6$ Da, in particular $1.0 \times 10^6$ Da to $3.0 \times 10^6$ Da or $1.5 \times 10^6$ Da to $2.5 \times 10^6$ Da. In case two different HAs are used, the first hyaluronic acid may have an average molecular weight of $1.0 \times 10^5$ Da to $5.0 \times 10^6$ Da, preferably $0.5 \times 10^6$ Da to $2.0 \times 10^6$ Da, more preferably $1.0 \times 10^6$ Da to $1.5 \times 10^6$ Da (or an intrinsic viscosity of 1.35 m$^3$/kg to 1.8 m$^3$/kg). The second hyaluronic acid has preferably an average molecular weight of greater than $1.0 \times 10^6$ Da up to $5.0 \times 10^6$ Da, in particular between $1.5 \times 10^6$ Da and $4.0 \times 10^6$ Da, preferably between $2.0 \times 10^6$ Da and $4.0 \times 10^6$ Da, and most preferably $2.8 \times 10^6$ Da to $3.2 \times 10^6$ Da (or 2.8 m$^3$/kg to 3.2 m$^3$/kg).

The crosslinked HA is preferably BDDE (1,4-butanediol diglycidyl ether)-crosslinked. The BDDE-crosslinked hyaluronic acid may have a degree of modification, expressed as the ratio of the sum of mono- and double-linked BDDE-cross-linkers to the sum of hyaluronic acid disaccharide units, of 0.5% to 25%, preferably 1.0% to 15%, more preferably 2.0% to 10%, and most preferably 3.0% to 8.0% or 4.0% to 7%.

The degree of modification can be determined by NMR in accordance with methods known in the art (Edsman et al., Gel Properties of Hyaluronic Acid Dermal Fillers, Dermatol. Surg. 2012, 38:1170-1179; Guarise et al., SEC determination of cross-link efficiency in hyaluronan fillers, Carbohydrate Polymers 2012, 88:428-434; Kenne et al., Modification and cross-linking parameters in hyaluronic acid hydrogels—Definitions and analytical methods, Carbohydrate Polymers 2013, 91:410-418).

In brief, the dialyzed and sterilized gels are degraded before conducting the NMR measurement. The degradation can be performed by chondroitinase AC (Edsman et al., supra; Kenne et al., supra), NaOH (Guarise et al., supra), addition of hyaluronidase (e.g., 150 U ovine hyaluronidase to 1 g of gel) or by incubation at 90° C. for at least 35 h. The obtained solutions are then lyophilized, dissolved in D$_2$O, and well homogenized.

The NMR measurement can be performed at, e.g., 500 MHz, at a pulse of 20 degree with several repetitions at ambient temperature to receive a spectrum with appropriate resolution. In accordance with the literature, the degree of modification (MoD) is assessed by calculating the ratio of the N-acetyl signals of HA to the methylene signals of BDDE. For N-acetyl of HA, the critical signals are located at about 2.0 ppm and at about 1.6 ppm for BDDE when solubilized in D$_2$O. In order to calculate the degree of modification, the integral values were identified and the ratio of protons of 3H of N-acetyl (CH$_3$) to 4H of methylene (CH$_2$CH$_2$) needs to be taken in account, in accordance with the literature (Edsman et al., supra, and Kenne et al., supra).

In accordance with the present invention, the HA derivative is present in the dermal filler composition at a concentration of at least 0.1%, e.g., 0.1% to 50%, preferably from 1.0% to 30%, more preferably from 5% to 25%, and most preferably from 10% to 20% by volume/volume. Alternatively, the HA derivative may be present in the dermal filler composition at a concentration of 0.001% to 2.0%, 0.01% to 1.0%, 0.05% to 0.5%, or 0.1% to 0.3% by weight/weight. Furthermore, the average molecular weight and viscosity of the HA derivative may be as defined hereinabove.

The dermal filler composition may further comprise one or more compounds selected from the group consisting of anesthetics, polyols, vitamins, amino acids, metals, antioxidants, hydroxyapatite particles, and mineral salts (e.g., a Zn salt). Preferably, the dermal filler composition comprises at least one local anesthetic agent, preferably lidocaine (e.g., lidocaine HCl). The local anesthetic, in particular lidocaine, may be present in the dermal filler composition in a concentration of, for example, 0.05 wt. % to 5.0 wt. %, 0.1 wt. % to 4.0 wt. %, 0.2 wt. % to 3.0 wt. %, 0.3 wt. % to 2.0 wt. %, or 0.4 wt. % to 1.0 wt. %.

Within the context of the present invention, the addition of a local anesthetic is particularly desirable in view of its ability to mitigate pain upon injection. Exemplary local anesthetic agents include, but are not limited to, ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dicyclomine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octocaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, and salts thereof.

Suitable polyols for use herein include, but are not limited to, glycerol, mannitol, sorbitol, propylene glycol, erythritol, xylitol, maltitol, and lactitol. Particularly suitable for use herein is mannitol and glycerol. Further, the polyol is preferably glycol, optionally in combination with one or more of the aforementioned polyol compounds, in particular mannitol. The polyol(s) may, for example, be included in the dermal filler composition in a concentration of 0.1% to 25% or 1% to 20% or 2% to 15% volume/volume, particularly in a concentration of 5% to 10% volume/volume.

Suitable vitamins include vitamin C, vitamin E and vitamins of the B group, i.e. one or more of $B_1$, $B_2$, $B_3$, $B_5$, $B_6$, $B_7$, $B_9$ and $B_{12}$ vitamins. The concentration of vitamin C or of vitamin E is preferably from about 0.01 mg/ml to about 10.0 mg/ml, more preferably from about 0.1 mg/ml to about 5.0 mg/ml, and the total concentration of the vitamins of the B group is preferably from about 0.01 mg/ml to about 10.0 mg/ml, more preferably from about 0.1 mg/ml to about 5.0 mg/ml. The vitamins may be present to stimulate and maintain cellular metabolism and, thus, to promote collagen production. Particularly preferred for use here is vitamin C, vitamin E and vitamin $B_6$.

It is further contemplated herein that the dermal filler composition may include non-crosslinked HA. In particular, the dermal filler composition may further comprise 0.001% to 15%, in particular 1% to 10% volume/volume non-crosslinked hyaluronic acid. The molecular weight of said non-crosslinked hyaluronic acid is preferably between $3.0 \times 10^5$ Da and $4.0 \times 10^6$ Da, in particular between $1.0 \times 10^6$ Da and $3.0 \times 10^6$ Da. Preferably, the dermal filler composition of the present invention lacks any crosslinked polymers other than the crosslinked HA described herein and, more preferably, also lacks any non-crosslinked polymers other than the HA derivative and/or the non-crosslinked (i.e. free) HA.

Furthermore, the dermal filler composition usually comprises a buffer, for example a phosphate buffer, to adjust the pH. The pH is generally in the range of 6.5 to 7.5, 6.5 to 7.4 or 6.5 to 7.1, or may be in the range of 6.8 to 7.4.

In a sixth aspect, the present invention relates to a method of preparing a dermal filler composition according to the present invention, comprising the steps of:
  (i) providing a hyaluronic acid (HA) derivative as defined in any one of claims 1 to 3,
  (ii) providing a crosslinked HA,
  (iii) combining the HA derivative and the crosslinked HA to obtain said dermal filler composition.

The method may further comprise a step of sterilizing the obtained dermal filler composition, optionally after having been filled into a syringe, preferably by moist heat such as by autoclaving.

In a seventh aspect, the present invention relates to a kit, comprising a dermal filler composition according to the present invention and, optionally, instructions for use. In a preferred embodiment, the kit comprises a syringe prefilled with the dermal filler composition of the present invention. The instructions for use preferably prescribe that the intended use of the kit is for cosmetic applications, in particular those described hereinbelow.

In an eighth aspect, the present invention relates to use of a dermal filler composition according to the present invention for cosmetic applications, e.g., for improving the visual appearance, in particular of the face. Cosmetic applications include, but are not limited to, augmenting or filling of wrinkles and lines of the skin, in particular of facial lines and facial wrinkles (e.g., glabellar lines, nasolabial folds, chin folds, marionette lines, buccal commissures, peri-oral wrinkles, and crow's feet). Other exemplary cosmetic applications include filling cutaneous depressions, masking scars and temples, providing subdermal support of the brows, malar and buccal fat pads, treating tear troughs, nose, chin and jawline corrections, increasing the volume of the lips, augmenting cheeks, treating the perioral region, infraorbital region and facial asymmetries, and/or improve skin hydration and skin texture.

In a ninth aspect, the present invention relates to a method for replacing or filling of a biological tissue or increasing the volume of the biological tissue for cosmetic purposes, comprising administering to a subject in need thereof an effective amount of the dermal filler composition according to the present invention.

The dermal filler composition of the present invention is generally administered in an effective amount to a subject by injection, such as by subcutaneous or intradermal injection. For example, the composition may be intradermally or subcutaneously injected using the serial puncture technique. The term "effective amount" refers to the amount of the (injectable) soft tissue filler composition sufficient to effect beneficial or desired cosmetic (aesthetic) or therapeutic results. A "subject" in the sense of the present invention is any individual or patient, usually a human, in need of the treatment of a particular condition or disease.

The present invention will now be further illustrated by the following, non-limiting example.

Examples

The following examples demonstrate that the glycerol-modified hyaluronic acid (HA) derivative of the present invention enables the preparation of a HA-based gel having superior physical (e.g., mechanical and rheological) properties.

Abbreviations

The following abbreviations are used throughout the section that follow:

| HA: | Hyaluronic acid | IF: | Injection force (extrusion force) [N] |
|---|---|---|---|
| G': | Storage (elastic) modulus [Pa] | G": | Loss (viscous) modulus [Pa] |
| tan δ: | Loss tangent = Tan Delta = G"/G' | μ: | Complex viscosity [Pa · s] |

Materials and Methods
Materials

Hyaluronic acid from bacterial fermentation (MW=$1.5 \times 10^6$ Da), 1 M HCl solution and 2 M NaOH solution, and glycidol were used in the experiments. Solvents and HA were used as received without any further purification or drying. All reactions were carried out under normal atmospheric conditions at room temperature unless otherwise noted.

NMR Measurements

NMR measurements were recorded on a Bruker spectrometer at room temperature. $^1$H NMR measurements were collected at 500 MHz. Chemical shifts (δ) (also referred to as signals or $^1$H NMR signals) are reported in parts per million (ppm). All spectra of HA and modified HA were recorded using measurement samples in a digested state. These digested measurement samples were prepared by precipitating the samples in isopropanol, drying the precipitated sample, subjecting the resulting sample to digestion using 50 U hyaluronidase at 40° C. for 12 h in aqueous solution, and finally freeze-drying the digested sample. Prior to NMR measurement the samples were solved in $D_2O$ to a concentration of about 20 mg/ml until homogeneity. NMR measurements were used to determine the degree of modification (MoD).

Rheological Measurements

Rheological measurements were performed using an Anton Paar MRC 302 rheometer (Anton Paar, Graz, Austria) equipped with a cone and plate geometry of 50 mm diameter and 1° angle, and a gap of 0.1 mm, at a frequency range of 10 to 0.1 Hz with a deformation of 0.1%. The rheological values indicated are at 1 Hz. All measurements were performed at a constant temperature of 25° C., unless otherwise stated.

Measurement of Extrusion Force

Extrusion force of gels was determined through a 30 G ½" needle (TSK Laboratory) at an extrusion rate of about 0.21 mm/sec using a standard 1.0 ml glass syringe (BD Hypak SCF, 1 ml long RF-PRTC, ISO 11040, inner diameter of 6.35 mm) using a Texture analyzer TA.XTPLUS.

Synthesis of Modified Hyaluronic Acid

The glycerol-modified HA derivative (Gly-HA) was synthesized by the following (hyper)grafting procedure. First, the raw material HA (having an intrinsic viscosity of 3.1 m$^3$/kg) is solubilized in water until full homogeneity. A sodium hydroxide solution was added. Then, glycidol was added, e.g., in an amount of 1.0 equivalent (mol/mol eq), calculated by the molecular mass (HA=402 g/mol, glycidol=74 g/mol), and reacted with the HA at about 50° C. for about 3 h to graft glycidol to the HA backbone and, optionally, grow the grafted side chain by the addition of excess glycidol monomers (to the glycidol grafted on the HA backbone). It is also possible to use milder reaction conditions of, e.g., 40° C. for about 1.5 h to 2.0 h. Alternatively, the raw material HA (e.g., dry HA fibers of 3.1 m$^3$/kg) may be added to an aqueous NaOH/glycidol solution, followed by reaction under the above-mentioned reaction conditions.

This "grafting from" type of reaction ultimately resulted in the generation of a linear-hyperbranched graft-copolymer (LHGC), i.e. a hyaluronic acid-graft-hyperbranched polyglycerol (HA-g-hbPG). The described synthesis pathway is illustrated in Scheme 1, infra.

Scheme 1

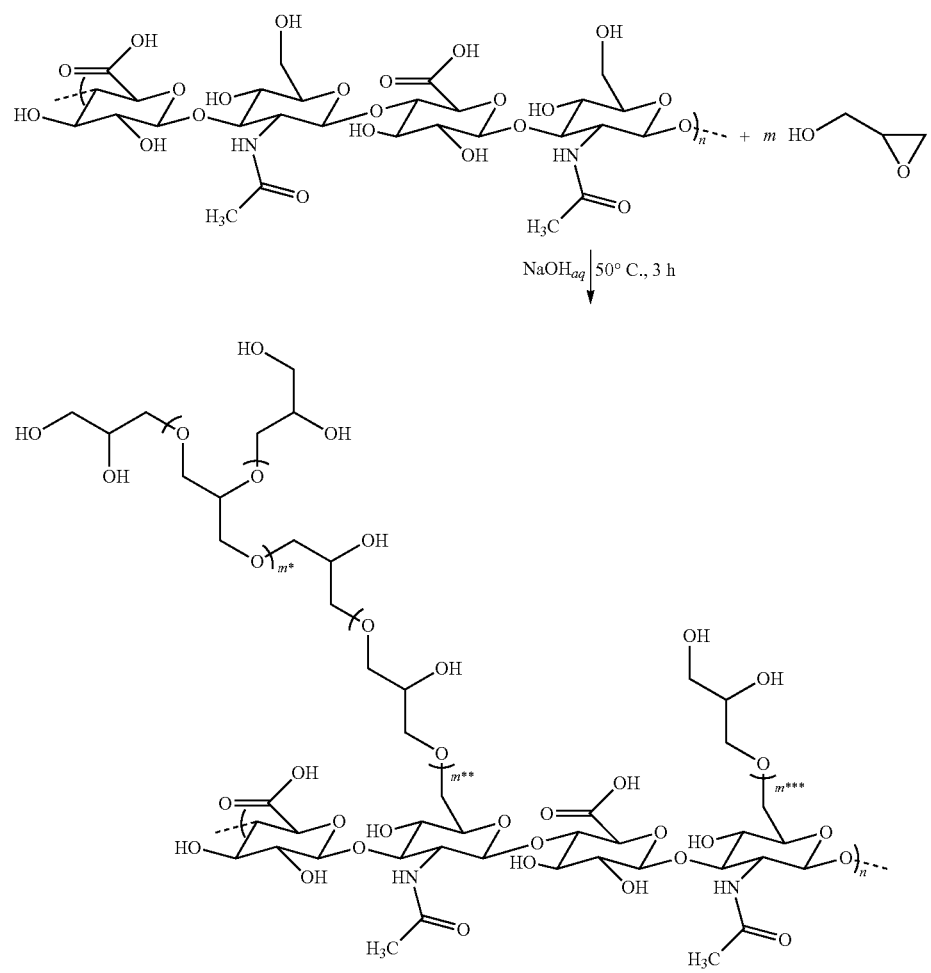

As can be seen, the "grafting from" approach results in glycerol-modified hyaluronic acid having dendrimeric, hyperbranched polyglycerol structures at the HA chain. The chain length n depends on the molecular weight of the raw material and the alkaline treatment conditions, whereas the units m of glycidol, which are either a terminal mono-ether m*, an intramolecular di-ether m or a intramolecular tri-ether m*, is a result of the stoichiometric ratio of glycidol to repeating disaccharide units of HA. The intended (poly) glycerol structure is referred to the amount of m*, whereas the units m and m* are essential to create and increase the amount of hydrogen acceptor and donor functionalities.

Since the most nucleophilic group of HA is the hydroxyl group at the C6 position of N-Acetyl-D-glucosamine (Glc-NAc), the (poly)glycerol structure is very likely formed at this position of the HA polymer. Due to its pKa the hydroxyl group at C6 is deprotonated first, compared to secondary OHs of the pyranose, and the dendrimeric (poly)glycerol is formed primarily at the C6 position. As soon as glycidol is added, the resulting alkoxide attacks the methylene carbon atoms of the oxirane ring of glycidol, resulting in ring-opening and formation of a new alcohol (or alkoxide) functional group (anionic ring-opening polymerization mechanism). The newly formed primary alcohol(ate) competes with the primary C6 alcohol(ate) group of HA and—due to the steric hindrance of the HA polymeric chain and the fixed structure of the pyranose—is believed to result in a growing polyglycerol structure on the initial glycidol moiety attached via the C6 position to the HA backbone.

The glycidol-HA reaction product was then neutralized (pH=7) using HCl, diluted and homogenized by stirring/dispersing. The product was then dehydrated by cycles of ethanol addition/sieving/pressing, followed by drying in an oven under vacuum and elevated temperature (45° C.).

In order to study the degree of modification of HA as a function of the employed amount of glycidol, the following glycidol-modified HA (Gly-HA) samples were prepared according to the synthesis procedure outlined above by using varying amounts of glycidol (see TABLE 1).

TABLE 1

Gly-HA samples S1 to S3

| Sample | Formulation |
| --- | --- |
| S1 | HA + 0.5 eq Gly (Gly-HA prepared using 0.5 equivalents glycidol) |
| S2 | HA + 1.0 eq Gly (Gly-HA prepared using 1.0 equivalents glycidol) |
| S3 | HA + 2.0 eq Gly (Gly-HA prepared using 2.0 equivalents glycidol) |

Manufacturing of Hydrogels

In order to study the influence of glycidol towards BDDE cross-linked HA hydrogels, four different HA-based hydrogels were prepared as summarized in TABLE 2.

In case of gel A, glycidol is added after pre-cross-linking of HA with BDDE in a one-step procedure.

Gel B is prepared according to prior art US 2010/0035838 A1, where BDDE and glycidol are added simultaneously to HA to create a cross-linked hydrogel (competitive conditions).

Gel C is manufactured in the same manner as a standard BDDE cross-linked HA hydrogel.

Gel D was prepared using the inventive procedure, whereas Gly-HA is added as separate phase to a final BDDE cross-linked HA hydrogel.

TABLE 2

HA-based hydrogels A to D

| Gel | Formulation/Conditions | Comments |
| --- | --- | --- |
| A | 9% BDDE + HA → 10 min cross-linking at 50° C. + 2.0 eq glycidol → 3 h 50 min of cross-linking and/or grafting at 50° C. | Pre-cross-linking is implemented to differentiate to prior art (1st step). Uncontrolled conditions of grafting and cross-linking in competitive reactions (2nd step). Represents a gel with a randomized cross-linked/grafted network. |
| B | 9% BDDE + HA + 2.0 eq glycidol → 4 h cross-linking | Comparison with prior art prior art (US 2010/0035838 A1) Competitive reaction: grafting and cross-linking or both |
| C | 9% BDDE + HA → 4 h cross-linking | Standard commercial BDDE cross-linked HA (reference) |
| D | Phase 1: 9% BDDE + HA → 4 h cross-linking Phase 2: 2.0 eq glycidol + HA → 4 h grafting Phase 3: mixture of phases 1 and 2 | Inventive sample Controlled conditions: separate cross-linking (Phase 1) and grafting (Phase 2). Controlled process with no competitive reaction. Enables proper adjustment of both phases and leads to predictable results. |

Results and Discussion

Grafting of Glycidol

The grafting of glycidol on HA was verified by proton nuclear magnetic resonance ($^1$H NMR) measurements. First, spiked cross-linked HA spectra were measured to check the presence of glycerol moieties as a result of the glycidol grafting. The decisive signals of glycerol can be found at 3.71 (d, J=4.3 Hz, 1H), 3.69 (s, 1H), 3.61 (d, J=6.5 Hz, 2H), 3.59 (d, J=6.5 Hz, 1H). The particular coupling and shift of these signals depend on the branching of the repeating units m (see Scheme 1, supra). Unfortunately, however, it was found that these characteristic signals fully overlap with the signals of the glycopyranose ring of the hyaluronic acid repeating units (results not shown).

A significant difference was only detectable when glycidol is added in sufficient amounts enabling the formation of hyperbranched structures. As a consequence, an absolute amount of grafting cannot be calculated based on the NMR data, but the incorporation of glycidol can be proven and calculated as a relative measure. Therefore, the NMR integration values of the glycidol-specific signals are the key parameters for confirming the successful grafting and the amount of polyglycerol structures present on the HA backbone.

More specifically, the recorded $^1$H NMR spectra were analyzed by comparing the decisive signals of the polyglycerol that are expected to occur at about 3.90 ppm-3.96 ppm (~3.90 ppm) and at about 3.60 ppm-3.55 ppm (~3.60 ppm), wherein the signal of the N-acetyl of HA (3H) at 2.08 ppm was set to 3.00. As a consequence of setting the 3H signal to 3.00, the signals of the anomeric protons at 4.62 and 4.51 (2H) were expected to give an integration value of about 2.00 and the signal at 3.40 ppm (1H) of the HA was expected to be about 1.00, due to the protons of the two monomer of HA. Further, the integrated values of the grafted-glycidol signals were expected to be higher, the higher the amount of grafted glycidol, while the integrated values of the signals attributable to the HA backbone should remain constant. As shown in TABLE 3, this was indeed observed for the three synthesized Gly-HA samples.

TABLE 3

NMR integration values of the relevant signals of the Gly-HA samples S1 to S3

| $^1$H NMR signals | S1 (HA + 0.5 eq Gly) | S2 (HA + 1.0 eq Gly) | S3 (HA + 2.0 eq Gly) |
|---|---|---|---|
| HA (3H, 2.08 ppm) | 3.00 | 3.00 | 3.00 |
| HA (1H, 3.40 ppm) | 1.20 | 1.22 | 1.12 |
| Gly-HA (~3.60 ppm) | 3.97 | 4.32 | 5.53 |
| Gly-HA (~3.90 ppm) | 3.03 | 3.32 | 3.73 |
| HA (2H, 4.55 ppm) | 2.07 | 2.11 | 2.03 |

Rheological Properties of Glycidol-Modified HA

The impact of glycidol-grafting was assessed by measuring the storage modulus G' and the complex viscosity p. The glycidol-modified HA samples (HA+0.5 eq, 1.0 eq or 2.0 eq glycidol) were prepared by subjecting the synthesized Gly-HA derivatives to exhaustive dialysis, followed by adjusting the concentration of the Gly-HA to 20 mg/ml. It was found that both the G' and µ are low (results not shown), which is believed to be the result of the alkaline (NaOH) degradation of the HA starting material. Therefore, variation of the pH, in particular lowering the pH to values below 10, is likely to limit glycosidic cleavage and, thus, provides an additional option to further modify the final properties of glycidol-modified HA.

Furthermore, a trend was observed in which higher amounts of glycidol used in the synthesis of the Gly-HA produced lower viscosity values (results not shown). Hence, variation of the pH of the alkaline degradation step and the amount of glycidol offers an optimization potential for creating dermal fillers having improved and/or fine-tuned properties.

Water-Binding Capacity of Glycidol-Modified HA

The water-binding capacity of glycidol-modified HA and native (i.e. "free", uncrosslinked or unmodified HA) was studied by means of dynamic vapor sorption using the instrument Dynamic Vapor Sorption Intrinsic from Surface Measurement Systems Ltd. The following samples were used:
  unmodified HA (degree of modification, MoD=0 mol %), and
  glycerol-modified HA (MoD=12.8 mol %).

The samples were dried overnight under vacuum at room temperature. To measure the water vapor sorption behavior, the samples were then exposed to atmosphere with increasing relative humidity at constant temperature (25° C.). Relative humidity was increased in 5% steps from 0% to 95%. At each step, the increase in the weight of the sample was measured after constant values were reached. Both samples were measured in duplicate and mean values were used for the analysis. An increase of the sample weight during the measurement indicates uptake of water from the atmosphere.

It was found that the glycerol modified hyaluronic acid takes up more water than native HA at high relative humidity (>85%; about 5-10% more at 90% relative humidity, and about 15-20% at 95% relative humidity). Thus, the modification with glycerol increases the ability of hyaluronic acid to bind water.

Rheological Properties of HA-Based Gels A to D

Four different gels (gels A, B, C and D as described above) were examined with respect to the impact of addition of glycidol-modified HA on the rheological properties of HA-based hydrogels. The results are shown in TABLE 4.

TABLE 4

Rheological properties of HA-based hydrogels A to D

| Gel | G' [Pa] | Viscosity [Pa*s] | IF [N] |
|---|---|---|---|
| A | 349.5 | 57.2 | 23.6 |
| B | 6.5 | 1.3 | 9.6 |
| C | 210.8 | 33.8 | 34.0 |
| D (inventive) | 172.3 | 27.8 | 17.1 |

The results demonstrate the difference in rheological properties of HA-based gels imparted by HA treated with BDDE and/or glycidol. A standard BDDE cross-linked HA gel as exemplified by gel C leads to a hydrogel with typical dermal filler properties. The presence of glycidol during the cross-linking reaction in the preparation of gel B interferes with the cross-linking process and thus significantly "weakens" the gel.

Additional treatment of BDDE cross-linked HA with glycidol in a consecutive reaction leads a "stronger" gel in terms of lifting capacity, as indicated by the increased G' value (see gel A). However, the competitive presence of glycidol and BDDE in case of gel A leads to undefined results, as BDDE has the ability to react with glycidol and/or HA. Hence an undesired undefined network is formed, which is essentially not reproducible and, thus, makes it impossible to establish a robust production process.

Admixing of a glycidol-modified HA derivative to a (pre-formed) standard BDDE cross-linked hydrogel, as in case of inventive gel D, results in a desirable lubrication effect, as indicated by a decreased injection force of 17.1 N, and an adequate complex viscosity similar to that of a standard BDDE cross-linked HA gel (see gel C).

Comparison of cHA/Gly-HA and cHA/Free HA Hydrogels in Terms of Injection Force, Storage Modulus and Loss Tangent The aim of this example was to assess the ability of uncrosslinked glycerol-modified HA (Gly-HA) to substitute for free HA (uncrosslinked HA) as lubricant in crosslinked HA-based gel formulations. To this extent, the injection force (IF), storage modulus (G') and loss tangent (tan δ=G"/G') were assessed.

The following samples were measured:
  BDDE-crosslinked HA hydrogel ("matrix"; Mw of HA=2.8 MDa)—no lubrication phase,
  "matrix" with 5% free HA (Mw=1.5 MDa) lubrication phase,
  "matrix" with 2% (w/w) Gly-HA lubrication phase,
  "matrix" with 5% (w/w) Gly-HA lubrication phase, and
  "matrix" with 8% (w/w) Gly-HA lubrication phase,
wherein the Gly-HA lubrication phase was prepared in accordance with the procedures outlined above (Mw=2.88 MDa, degree of modification (MoD): 11.8, intrinsic viscosity: 1.9 m$^3$/kg, complex viscosity (20 mg/ml in H$_2$O at 1 Hz): 28 Pa·s).

The results of the injection force and rheological measurements are shown in TABLE 5. As can be seen, the injection force (IF) for the pure matrix without lubrication phase ("Lub") is much higher than that observed for the matrix with lubrication phase. Furthermore, the same low injection force, i.e. the same lubrifying effect, was observed for free HA and Gly-HA at 5% (w/w). If 2% (w/w) of Gly-HA were used, the injection force was somewhat increased, whereas 8% (w/w) of Gly-HA resulted in a slightly decreased injection force. Thus, there appears to exist an inverse linear correlation between the content of Gly-HA in the matrix and the injection force (or lubrifying effect).

TABLE 5

Comparison of free HA and Gly-HA on the mechanical and rheological properties of a cHA-based gel

|  | IF [N] | G' [Pa] | Tanδ |
|---|---|---|---|
| Matrix (pure) - no Lub | 48.0 | 234 | 0.12 |
| Matrix + 5% free HA Lub | 18.1 | 193 | 0.19 |
| Matrix + 5% Gly-HA Lub | 18.2 | 194 | 0.19 |
| Matrix + 2% Gly-HA Lub | 25.3 | 214 | 0.16 |
| Matrix + 8% Gly-HA Lub | 13.0 | 177 | 0.23 |

As can be further seen from TABLE 5, like free HA, Gly-HA results only in a relatively low decrease of the storage modulus (or elastic modulus) G'. In fact, at 5% (w/w), G' is essentially identical for free HA and Gly-HA. Moreover, the addition of 5% Gly-HA resulted in a relatively small increase of loss tangent (tan δ). The increase of tan δ was found to be identical in case of free HA and Gly-HA.

These results demonstrate the equality of Gly-HA compared to free HA with respect to its intended use as lubrication agent. Accordingly, the mechanical and physical properties imparted by Gly-HA were comparable to those imparted by free HA, while Gly-HA additionally offers superior water binding affinity due to its polyglycerol structures grafted to the HA backbone.

Enzymatic Degradation of Glycidol-Modified HA and HA-Based Gels Containing Glycidol-Modified HA The potential for enzymatic degradation of glycidol-modified HA (Gly-HA) and for a HA filler formulation containing Gly-HA as lubrication phase was studied in comparison to unmodified (or "free") HA and a HA filler formulation containing free HA (or "native HA") as lubrication phase. The following samples were used:

glycerol-modified HA (Mw=1.7 MDa; MoD: 15 mol %); 20 mg/ml in 0.9% NaCl solution free HA (Mw=1.3 MDa; MoD: 0 mol %); 20 mg/ml in 0.9% NaCl solution cHA/GmHA gel: BDDE-crosslinked HA with uncrosslinked glycerol-modified HA lubrication phase cHA/free HA gel: BDDE-crosslinked HA with uncrosslinked glycerol-modified HA lubrication phase The rigidity of the hydrogel as assessed by measuring the storage modulus G' is used to monitor the digestion process over time. The enzymatic degradation is triggered by hyaluronidase which catalyzes the hydrolysis of 1,4-glycosidic linkages in HA. The experiments were carried out using an Anton Paar MCR 302 Rotational Rheometer (deformation 0.1%, temperature 36° C., frequency 1.0 Hz). 500 mg hydrogel were digested with 50 U hyaluronidase solubilized in 150 µL of water for injection. Measurements were carried out in duplicate and average values are reported for analysis.

It was surprisingly found that the enzymatic degradation of Gly-HA is comparable to that of native HA having a similar molecular weight (results not shown). Likewise, the two gel formulations of BDDE-crosslinked HA with native or Gly-HA as lubrication phase show a similar enzymatic degradation behavior. Accordingly, the enzymatic degradation of glycerol-modified HA is possible within the same time frame as for native hyaluronic acid.

Thermal Stability of HA-Based Gel Formulation Containing Glycerol-Modified HA as Lubricant To check the influence of glycerol-modified-HA ("Gly-HA") as lubrication phase compared to uncrosslinked (or "free") HA on the stability of a crosslinked HA (cHA) formulation, rheological data before and after sterilization of the gel and data from stability studies at 40° C. (1 and 3 months) were evaluated. The rheological measurements were carried out using an Anton Paar MCR 302 Rotational Rheometer. The storage modulus G' was measured in duplicate at 25° C., using deformation of 0.1% and frequency of 1 Hz. The following samples were examined:

cHA/free HA: 1.805% (w/w) BDDE-crosslinked HA plus 0.095% (w/w) uncrosslinked HA (Batches 1, 2 and 3), and cHA/free Gly-HA: 1.805% (w/w) BDDE-crosslinked HA plus 0.095% (w/w) uncrosslinked Gly-HA)

It was found that the drop of the storage modulus G' after the sterilization process (127° C., 6.5 min) is roughly 50% and similar for both examined formulations (see TABLE 5). Likewise, the 1 and 3 months stability studies resulted in a similar drop in G'. In sum, the data obtained show that the glycerol-modified lubrication phase exerts essentially the same beneficial effects as free HA on the stability of the formulation (see TABLE 6).

TABLE 6

Rheological properties of HA-based hydrogels with uncrosslinked HA or uncrosslinked Gly-HA

| Parameter measured | cHA/free HA | | | cHA/free Gly-HA | | |
|---|---|---|---|---|---|---|
|  | Batch 1 | Batch 2 | Batch 3 | Batch 1 | Batch 2 | Batch 3 |
| G' before steril. [Pa] | 433 | 475 | 460 | 414 | 443 | 427 |
| G' after steril. [Pa] | 199 | 228 | 214 | 200 | 225 | 208 |
| G' drop % after sterilization | 54 | 52 | 53 | 52 | 49 | 51 |
| Stability after 1 month at 40° C. | 174 | 207 | 188 | 179 | 203 | 188 |
| Stability after 3 months at 40° C. | 165 | 194 | — | 167 | 195 | — |
| G' drop % stability 1 month | 12.6 | 9.0 | 12.3 | 10.9 | 9.8 | 9.4 |
| G' drop % stability 3 months | 17.0 | 14.9 | — | 16.5 | 13.7 | — |

The experimental results presented above show that the addition of a glycidol-modified hyaluronic acid derivative to conventional BDDE cross-linked HA gels is a promising approach for the development of novel dermal fillers having superior physical, mechanical and rheological properties.

The invention claimed is:

1. An un-crosslinked glycerol-modified hyaluronic acid (HA) derivative or a salt thereof having at least the primary hydroxyl group at the C6 carbon atom of all or a part of the N-acetyl-D-glucosamine units of HA modified into ether-bonded glycerol-containing moieties.

2. The HA derivative of claim 1, wherein said glycerol-containing moiety that is bonded to the C6 carbon atom of HA via an ether bond is a single glycerol residue or a polyglycerol structure of two or more multi-ether-bonded glycerol residues.

3. The HA derivative of claim 1, wherein the HA derivative is HA or a salt thereof having an average molecular weight of $1.0 \times 10^4$ Da to $4.0 \times 10^6$ Da and/or wherein the glycerol-containing moieties are linked to the C6 carbon atom of N-acetyl-D-glucosamine units of HA in an amount such that said derivative comprises between 1 and 100 of said glycerol-containing moieties per 100 repeating disaccharide unit of the HA.

4. The HA derivative of claim 1, wherein said glycerol-containing moiety that is bonded to the C6 carbon atom of HA via an ether bond is a dendrimetric hyperbranched polyglycerol structure.

5. The HA derivative of claim 1, wherein the HA derivative is HA or a salt thereof having an average molecular weight of $1.0 \times 10^4$ Da to $4.0 \times 10^6$ Da and/or wherein the glycerol-containing moieties are linked to the C6 carbon atom of N-acetyl-D-glucosamine units of HA in an amount such that said derivative comprises between 5 and 50 of said glycerol-containing moieties per 100 repeating disaccharide unit of the HA.

6. A dermal filler composition comprising crosslinked hyaluronic acid (HA) or a salt thereof and the HA derivative or a salt thereof as defined in claim 1.

7. The dermal filler composition of claim 6, wherein the crosslinked HA is present at a concentration of 0.1% to 4.0% by weight/volume and/or wherein the HA derivative is present at a concentration of 0.1% to 30.0% by volume/volume.

8. The dermal filler composition of claim 6, wherein the crosslinked HA is crosslinked with 1,4-butanediol diglycidyl ether (BDDE).

9. The dermal filler composition of claim 6, further comprising one or more compounds selected from the group consisting of anesthetics, polyols, vitamins, amino acids, metals, antioxidants, hydroxyapatite particles, and mineral salts, wherein the composition optionally comprises a local anaesthetic agent optionally lidocaine.

10. The dermal filler composition of claim 6, wherein the crosslinked HA is present at a concentration of 1.0% to 3.0% by weight/volume and/or wherein the HA derivative is present at a concentration of 5% to 25% by volume/volume.

11. A kit, comprising a dermal filler composition according to claim 6 and, optionally, instructions for use.

12. A method for making a hyaluronic acid (HA) derivative or a salt thereof as defined in claim 1, comprising:
 (a) solubilizing HA in an aqueous alkaline solution to obtain solubilized HA,
 (b) adding glycidol to the solubilized HA of (a),
 (c) reacting glycidol and HA to obtain a glycerol-modified HA derivative and,
 (d) isolating the glycerol-modified HA derivative.

13. The method of claim 12, wherein (d) comprises the following:
 (d1) neutralizing a reaction mixture resulting from (c) comprising the glycerol-modified HA derivative, and
 (d2) isolating the glycerol-modified HA derivative from the neutralized reaction mixture to obtain the glycerol-modified HA derivative, or a salt thereof, in purified form.

14. A method of preparing a dermal filler composition as defined in claim 6, comprising:
 (i) Providing the hyaluronic acid (HA) derivative or a salt thereof,
 (ii) providing a crosslinked HA or a salt thereof,
 (iii) combining the HA derivative or a salt thereof and the crosslinked HA or a salt thereof to obtain said dermal filler composition.

15. A method of cosmetic treatment comprising administering to a subject an effective amount of the dermal filler composition according to claim 6.

16. A method for replacing or filling of a biological tissue or increasing the volume of the biological tissue for cosmetic purposes, comprising administering to a subject in need thereof an effective amount of the injectable dermal filler composition according to claim 6.

17. The method of cosmetic treatment according to claim 16, wherein the cosmetic treatment comprises treatment of facial lines, facial wrinkles, glabellar lines, nasolabial folds, marionette lines, buccal commissures, peri-lip wrinkles, crow's feet, subdermal support of the brows, malar and buccal fat pads, tear troughs, nose, lips, cheeks, peroral region, infraorbital region, facial asymmetries, jawlines, or chin.

* * * * *